US00PP09724P

United States Patent [19]

VandenBerg

[11] Patent Number: Plant 9,724

[45] Date of Patent: Dec. 3, 1996

[54] CARNATION PLANT NAMED MONICA

[75] Inventor: Cornelis P. VandenBerg, Salinas, Calif.

[73] Assignee: Yoder Brothers, Inc., Barberton, Ohio

[21] Appl. No.: 513,521

[22] Filed: Aug. 10, 1995

[51] Int. Cl.[6] ..... A01H 5/00

[52] U.S. Cl. ..... Plt./70.7

[58] Field of Search ..... Plt./70.7

*Primary Examiner*—James R. Feyrer

*Attorney, Agent, or Firm*—Foley & Lardner

[57] ABSTRACT

A carnation plant named Monica particularly characterized by its commercial double flower type; flat, high centered flower form; red flower color; diameter of flower of 55 to 58 mm when fully opened, when grown as a spray carnation; petal margins are slightly serrated and ruffled; strong, flexible stems; high production of flowering stems per plant; high production of flowers, with 5 to 7 flowering laterals developing per stem; flowering response of 26 weeks after planting rooted cuttings; very resistant to *Fusarium oxysporum*; and recommended as a miniature (spray) carnation.

2 Drawing Sheets

The present invention comprises a new and distinct cultivar of carnation, botanically known as *Dianthus caryophyllus* L. and referred to by the cultivar name Monica.

Monica, identified as 2066 (85-084021), was originated from a cross made under supervision of Cornelis P. VandenBerg in a controlled breeding program in Salinas, Calif., in 1984.

The female parent of Monica was the cultivar identified as Etna, a red spray carnation.

The male parent of Monica was the cultivar identified as Starlight, also a red spray carnation.

The breeding program resulting in Monica had the objective of creating new carnation cultivars resistant to *Fusarium oxysporum*. In order to ensure resistance, seedlings were planted in a controlled environment in soil heavily infested with *Fusarium oxysporum* in Suba, near Bogota, Colombia. Seedlings were allowed to grow for 18 months, with removal of those seedlings that died from *Fusarium oxysporum*.

Monica was discovered and selected as one flowering plant within the progeny of the stated cross by Cornelis P. VandenBerg in Oct. 1986, in the above-described location.

The first act of asexual reproduction of Monica was accomplished when vegetative cuttings were taken from the initial selection in Suba, Colombia, in October 1986, immediately after selection, by technicians working under supervision of Cornelis P. VandenBerg.

Horticulture examination of controlled flowerings of successive plantings has shown that the unique combination of characteristics as herein disclosed for Monica are firmly fixed and are retained through successive generations of asexual reproduction.

Monica has not been observed under all possible environmental conditions. The phenotype may vary significantly with variations in environment such as temperature, light intensity and daylength, without, however, any variance in genotype.

The following observations, measurements and comparisons describe plants grown in Suba near Bogota, Columbia, under greenhouse conditions which approximate those generally used in commercial greenhouse practice.

The following traits have been repeatedly observed and are determined to be basic characteristics of Monica, which, in combination, distinguish this carnation as a new and distinct cultivar:

1. Commercial double flower type.
2. Flat, high centered flower form.
3. Red flower color.

4. Diameter of flower of 55 to 58 mm when fully opened, when grown as a spray carnation.
5. Petal margins are slightly serrated and ruffled.
6. Strong, flexible stems.
7. High production of flowering stems per plant.
8. High production of flowers, with 5 to 7 flowering laterals developing per stem.
9. Flowering response of 26 weeks after planting rooted cuttings.
10. Very resistant to *Fusarium oxysporum.*
11. Recommended as a miniature (spray) carnation.

The accompanying photographic drawings show typical inflorescence of Monica, with the colors being as nearly true as possible with illustrations of this type.

Sheet 1 is a color photograph of Monica grown as a spray cut carnation.

Sheet 2 is a black and white photograph of three views of the inflorescence of Monica. In sheet 2 a measuring tape in centimeters has been added.

The combination of red flower color, high production of flowering stems per plant, high production of flowers per stem and very high resistance to *Fusarium oxysporum* is not represented in any commercial spray carnation cultivar known to the inventor.

In the following description color references are made to The Royal Horticultural Society Colour Chart. The color values were determined on plant material grown as spray carnations in Salinas, Calif. on Jun. 5, 1992.

Classification:

*Botanical.*—*Dianthus caryophyllus* L. cv Monica.

*Commercial.*—Spray carnation for cut flower production.

INFLORESCENCE

Capitulum:

*Form.*—Flat, high centered.

*Type.*—Commercial double.

*Flower diameter.*—55 to 58 when fully opened.

*Number of petals.*—55 to 65.

*Color (general tonality from a distance of three meters).*—Red.

*Color (upper surface).*—Between 45A to 45B and 46B. Color is table during maturity.

*Shape.*—Rounded, slightly serrated and ruffled.

*Androecium.*—Normal to semi-petaloid stamens; normal to degenerated anthers; moderate pollen.

*Gynoecium.*—Typical carnation, smooth, conical ovaries, three styles.

*Fragrance.*—Very slight, typical carnation.

*Fertility.*—Functions weakly as both male and female parent.

*Keeping quality.*—7 to 14 days after cutting.

PLANT

General appearance:

*Growth.*—Bushy, semi-erect perennial; plant is normally pinched approximately three weeks after planting to produce upright habit typical of cut carnations.

*Branching pattern.*—Semi-erect, numerous and unrestricted at base of plant; 5 to 7 flowering laterals developing per stem.

*Height.*—Two (2) year old plants may reach 150 to 200 cm in height.

Foliage:

*Color.*—Typical carnation, closest to 189A overlaid with 189B.

*Texture.*—Surface has a thin wax-like finish which is bluish green in color.

*Size.*—Mature leaves are 10 to 16 cm in length and 7 to 10 mm in width; weakly curled.

*Shape.*—Long, narrow, lancet shaped.

*Flowering.*—The first flush of flowers appears 26 weeks after planting rooted cuttings, and there are approximately 5 to 7 flowering stems at first flush when the apical bud is removed. The side laterals then grow out in approximately 8 weeks, after which the second flush of flowers appears. The flowers of the first and second flushes are similar in size, but in subsequent flushes the flowers tend to become somewhat smaller. There are approximately 6 to 8 flushes of flowers during a two year plant life, at which time a commercial plant would typically be discarded.

It is claimed:

1. A new and distinct carnation plant named Monica, as described and illustrated.

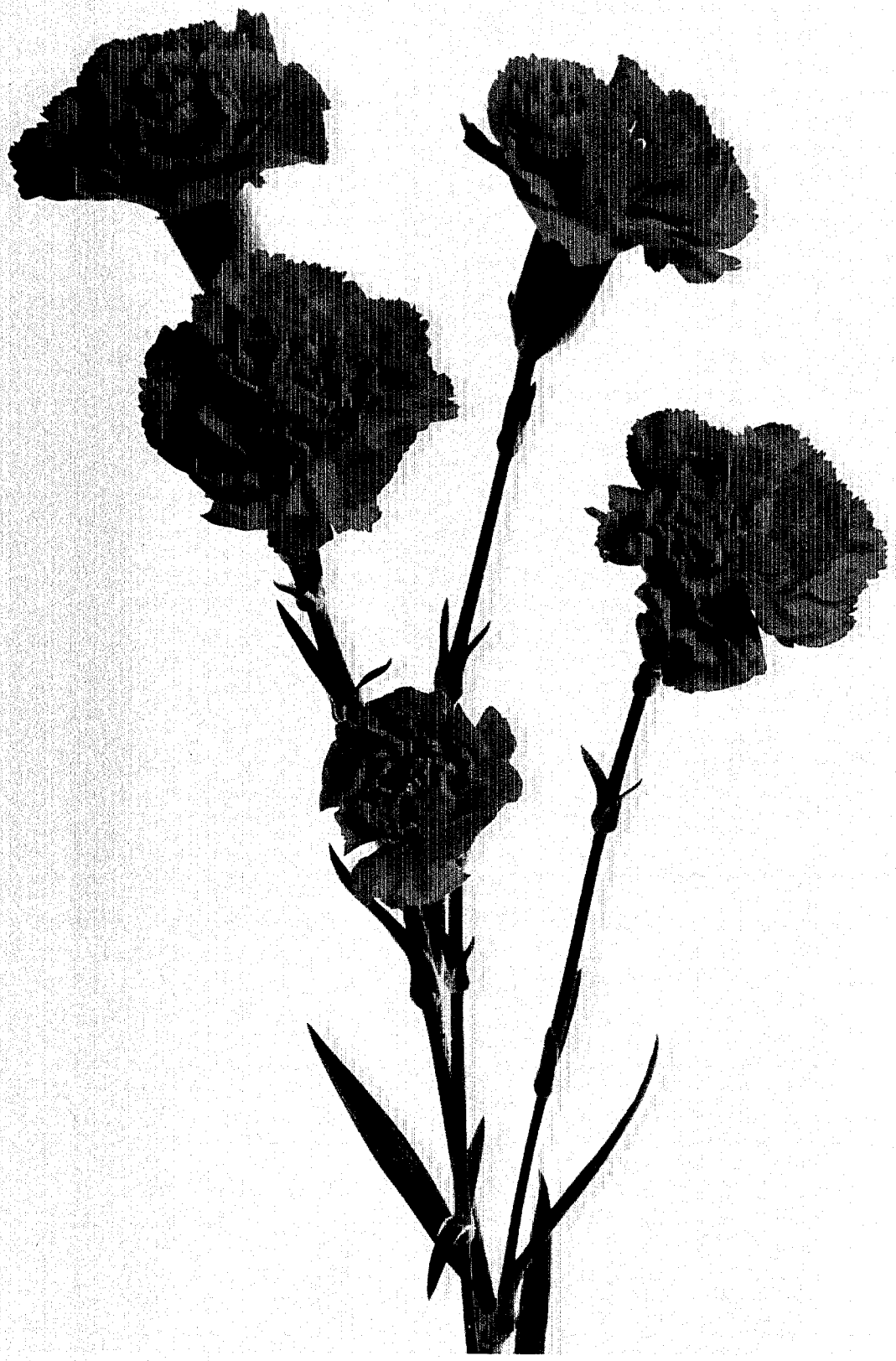

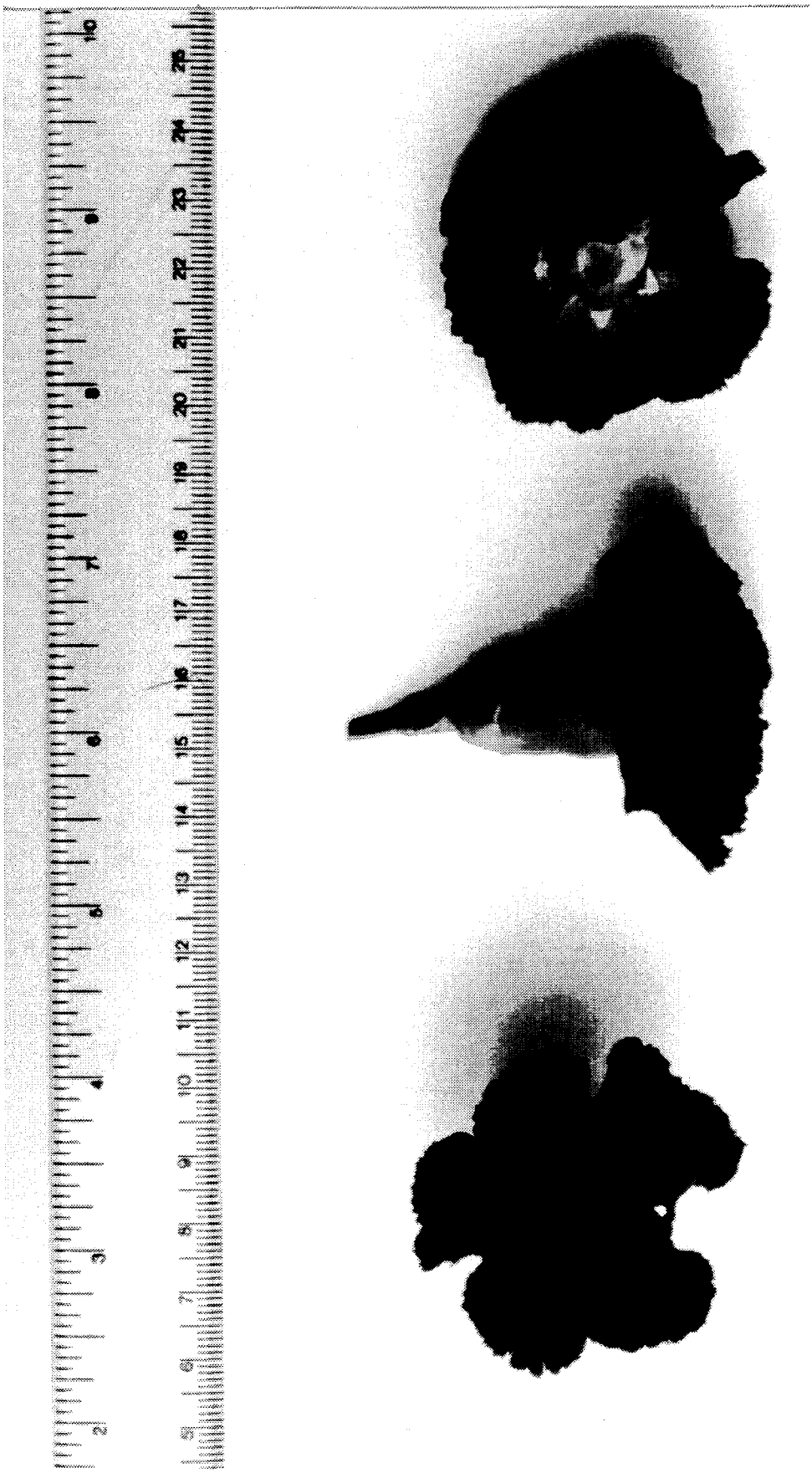

* * * * *